(12) United States Patent
Molla et al.

(10) Patent No.: US 12,234,724 B2
(45) Date of Patent: Feb. 25, 2025

(54) DETERMINING HYDROCARBON RESOURCE CHARACTERISTICS VIA MUD LOGGING

(71) Applicant: Schlumberger Technology Corporation, Sugar Land, TX (US)

(72) Inventors: Shahnawaz Hossain Molla, Cambridge, MA (US); Maneesh Pisharat, Aberdeen (GB); Yujian Wu, Dove, NH (US); Farshid Mostowfi, Lexington, MA (US); Oscar Eduardo Torres Jaimes, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1088 days.

(21) Appl. No.: 17/010,368

(22) Filed: Sep. 2, 2020

(65) Prior Publication Data

US 2021/0062650 A1   Mar. 4, 2021

Related U.S. Application Data

(60) Provisional application No. 62/940,974, filed on Nov. 27, 2019, provisional application No. 62/895,578, filed on Sep. 4, 2019.

(51) Int. Cl.
*E21B 49/08* (2006.01)
*E21B 21/06* (2006.01)
(Continued)

(52) U.S. Cl.
CPC ........ *E21B 49/0875* (2020.05); *E21B 21/067* (2013.01); *E21B 49/005* (2013.01);
(Continued)

(58) Field of Classification Search
CPC .. E21B 49/0875; E21B 21/067; E21B 49/005; E21B 49/084; E21B 49/086;
(Continued)

(56) References Cited

U.S. PATENT DOCUMENTS 6,443,001 B1   9/2002   Duriez et al.
7,392,138 B2   6/2008   Frechin et al.
(Continued)

FOREIGN PATENT DOCUMENTS

WO   WO-2014196979 A1 * 12/2014  ............ G01N 21/31
WO   2020185094 A1   9/2020

OTHER PUBLICATIONS

Copping, Simon, Jason Payne, and Ronan O'Malley. "Leveraging Data Analytics to Optimise Production Performance." SPE Asia Pacific Oil and Gas Conference and Exhibition. OnePetro, 2018. (Year: 2018).*

(Continued)

*Primary Examiner* — John E Johansen

(57) ABSTRACT

Methods (and related apparatus) include obtaining data regarding a measured property. The measured property includes an amount of each of predetermined hydrocarbons in a gas sample extracted from drilling fluid exiting a wellbore having a hydrocarbon resource. An unknown characteristic of an investigated fluid property of the hydrocarbon resource is predicted utilizing the obtained input data and one or more predetermined models each built via statistical classification and regression analysis of a preexisting database containing records. Each record includes known characteristics of fluid properties of a different one of known reservoir fluids. The fluid properties include the investigated fluid property and the measured property. The investigated fluid property includes a fluid type of the
(Continued)

hydrocarbon resource, an amount of at least one additional hydrocarbon, gas-oil ratio, or stock tank oil density.

20 Claims, 9 Drawing Sheets

(51) Int. Cl.
E21B 49/00 (2006.01)
G01N 33/28 (2006.01)
(52) U.S. Cl.
CPC .......... *E21B 49/084* (2013.01); *E21B 49/086* (2013.01); *E21B 49/088* (2013.01); *G01N 33/2823* (2013.01); *E21B 2200/20* (2020.05); *E21B 2200/22* (2020.05)
(58) Field of Classification Search
CPC ............... E21B 49/088; E21B 2200/20; E21B 2200/22; G01N 33/2823
USPC .......................................................... 703/10
See application file for complete search history.

(56) References Cited

U.S. PATENT DOCUMENTS

| 2011/0303463 | A1 | 12/2011 | Lessi | |
|---|---|---|---|---|
| 2017/0328202 | A1* | 11/2017 | Hsu | E21B 49/10 |
| 2018/0088096 | A1 | 3/2018 | Ritzmann | |
| 2022/0163503 | A1* | 5/2022 | Yang | G01V 9/007 |

OTHER PUBLICATIONS

Trivedi, Shubhendu, Zachary A. Pardos, and Neil T. Heffernan. "The utility of clustering in prediction tasks." arXiv preprint arXiv: 1509.06163 (2015). (Year: 2015).*
Bandura, Laura, Adam D. Halpert, and Zhao Zhang. "Machine learning in the interpreter's toolbox: Unsupervised, supervised, and deep-learning applications." SEG International Exposition and Annual Meeting. SEG, 2018. (Year: 2018).*
European Search Report dated Jan. 15, 2021 in European Application No. 20194064.0.
Merino-Garcia et al "An Innovative Approach for Formation Fluid Typing with API and GOR Assessments in Real Time from Mud Gas Data," 76th EAGE Conference & Exhibition, Jun. 19, 2014, pp. 16-19.
François Montel "Phase Equilibria Needs for Petroleum Exploration and Production Industry", Fluid Phase Equilibria, vol. 84, 1993, pp. 343-367.
Communication Pursuant to Rule 114(2) EPC issued in European Patent Application No. 20194064.0 dated Jun. 23, 2023, 9 pages.
Fong, D. "Predicting Stock Returns with Cluster-Then-Predict", Mar. 29, 2019, Homework assignment for MITx "The Analytics Edge", 15 pages.
Trivedi, S. et al., "The Utility of Clustering in Prediction Tasks", An experimental research report, Sep. 2011, 11 pages.
Summons to Attend Oral Proceedings pursuant to Rule 115(1) EPC issued in European Patent Application No. 20194064.0 dated Jul. 10, 2023, 14 pages.
Ali et al., Prediction of Reservoir Fluid Facies Through Collaborative Workflow of Advanced Surface and Downhole Methodology, in Abu Dhabi International Petroleum Exhibition Conference. Nov. 2017, Society of Petroleum Engineers: Abu Dhabi, UAE. 12 pages.
Fornasier et al., The Essential Role of the Advanced Surface Fluid Logging in the Reservoir Fluid Evaluation Workflow, in SPWLA 56th Annual Logging Symposium. 2015, Society of Petrophysicists and Well-Log Analysts: Long Beach, California, USA, Jul. 2015, 17 pages.
Haworth et al., Reservoir Characterization by Analysis of Light Hydrocarbon Shows, SPE12914, SPE Rocky Mountain Regional Meeting, May 21-23, 1984, Casper, Wyoming, 6 pages.
Kyi et al., Integration of Downhole Fluid Analysis and Advanced Mud Gas Logging Reduces Uncertainty in Reservoir Evaluation, International Petroleum Technology Conference, Jan. 2014, Doha, Qatar, 13 pages.
Pixler, B.O., Formation Evaluation by Analysis of Hydrocarbon Ratios, Journal of Petroleum Technology, Jun. 1969. 21(06) pp. 665-670.
Rane et al., Realtime Reservoir Fluid Characterization Using High Efficiency Gas Extraction Membrane Technology System and Advanced GC Tracer Chromatograph; A Case Study from East Kuwait Jurassic Reservoir, in SPE Kuwait Oil Gas Show and Conference Oct. 2017, Society of Petroleum Engineers: Kuwait City, Kuwait 23 pages.
Ritzmann et al., Distinguishing In-Place Hydrocarbons from OBM Invasion by Integrating Conventional and Advanced Formation Evaluation Workflows with a New, Innovative Gas Ratio Analysis Approach, in SPWLA 57th Annual Logging Symposium Jun. 2016, Society of Petrophysicists and Well-Log Analysts: Reykjavik, Iceland 13 pages.
Rochon, R.W., Can In-situ Reservoir Hydrocarbon Composition Be Predicted From Hydrocarbon Analysis of The Mud Stream The Log Analyst, Jan.-Feb. 1978. 19(01) 18 pages.
Wilson, T., The Quantification Of Mud Log Gas Shows, in SPWLA 17th Annual Logging Symposium. Jun. 1976, Society of Petrophysicists and Well-Log Analysts: Denver, Colorado. 10 pages.
Wright, A. C., Estimation Of Gas/Oil Ratios And Detection Of Unusual Formation Fluids From Mud Logging Gas Data, in SPWLA 37th Annual Logging Symposium. Jun. 1996, Society of Petrophysicists and Well-Log Analysts: New Orleans, Louisiana, 14 pages.
Yang et al., A Machine Learning Approach to Predict Gas Oil Ratio Based on Advanced Mud Gas Data, SPE-195459, in SPE Europec featured at 81st EAGE Conference and Exhibition. Jun. 2019, Society of Petroleum Engineers: London, England, UK. 17 pages.
Communication Pursuant to Rule 94(3) EPC issued in European Patent Application No. 20194064.0 dated Dec. 16, 2022, 11 pages.
Communication Pursuant to Rule 114(2) EPC issued in European Patent Application No. 20194064.0 dated Oct. 13, 2022, 8 pages.
Hastie, T., R. Tibshirani, and J. Friedman, The Elements of Statistical Learning. Springer Series in Statistics. 2009: Springer-Verlag New York, Chapter 1—p. 1, Section 2.1 2.2 p. 9.
James, G., et al., An Introduction to Statistical Learning with Applications in R. Springer Texts in Statistics. 2013: Springer-Verlag New York. Section 2.1—p. 15.

\* cited by examiner

DETERMINING HYDROCARBON RESOURCE CHARACTERISTICS VIA MUD LOGGING

CROSS-REFERENCE TO RELATED APPLICATIONS

This application claims priority to and the benefit of U.S. Provisional Application No. 62/895,578, titled "Fluid-type identification from advanced mud gas analysis data using machine learning techniques," filed Sep. 4, 2019, and U.S. Provisional Application No. 62/940,974, titled "Method For Determining One Or More Properties Of A Geological Formation Using Mud Logging Gas Data," filed Nov. 27, 2019, the entire disclosures of which are hereby incorporated herein by reference.

BACKGROUND OF THE DISCLOSURE

In the oil and gas industry, from exploration to production, the uncertainty associated with the value of hydrocarbon resources may be sought for various reasons. Analysis of gas in drilling fluid ("mud") during drilling may produce the earliest information about such hydrocarbon resources. Variation in gas concentrations in the drilling mud is controlled by numerous factors and can be broadly attributed to drilling parameters, environment changes, formation fluid changes, and drilling fluid changes. Due to these limiting factors, existing analysis methodology is primarily focused on establishing qualitative results.

SUMMARY OF THE DISCLOSURE

This summary is provided to introduce a selection of concepts that are further described below in the detailed description. This summary is not intended to identify indispensable features of the claimed subject matter, nor is it intended for use as an aid in limiting the scope of the claimed subject matter.

The present disclosure introduces a method that includes obtaining input data regarding at least one measured property. The at least one measured property includes an amount of each of predetermined hydrocarbons in a gas sample extracted from drilling fluid after the drilling fluid exits a wellbore. The wellbore penetrates a subterranean formation having a hydrocarbon resource. The method also includes predicting an unknown characteristic of an investigated fluid property of the hydrocarbon resource utilizing the obtained input data and one or more predetermined models each built via statistical classification and regression analysis of a preexisting database containing records. Each record includes known characteristics of fluid properties of a different one of known reservoir fluids. The fluid properties include the investigated fluid property and the at least one measured property. The investigated fluid property includes at least one of a fluid type of the hydrocarbon resource, an amount of at least one additional hydrocarbon, gas-oil ratio (GOR), or stock tank oil (STO) density.

The present disclosure also introduces a system that includes a processing system having a processor and memory storing program code instructions executable by the processor to receive input data regarding at least one measured property. The at least one measured property includes an amount of each of hydrocarbons in a gas sample extracted from drilling fluid after the drilling fluid exits a wellbore. The wellbore penetrates a subterranean formation having a hydrocarbon resource. The instructions are also executable by the processor to predict an unknown characteristic of an investigated fluid property of the hydrocarbon resource utilizing the obtained input data and one or more predetermined models each built via statistical classification and regression analysis of a preexisting database containing records. Each record includes known characteristics of fluid properties of a different one of known reservoir fluids. The fluid properties include the investigated fluid property and the at least one measured property. The investigated fluid property includes at least one of a fluid type of the hydrocarbon resource, an amount of at least one additional hydrocarbon, GOR, or STO density.

These and additional aspects of the present disclosure are set forth in the description that follows, and/or may be learned by a person having ordinary skill in the art by reading the material herein and/or practicing the principles described herein. At least some aspects of the present disclosure may be achieved via means recited in the attached claims.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
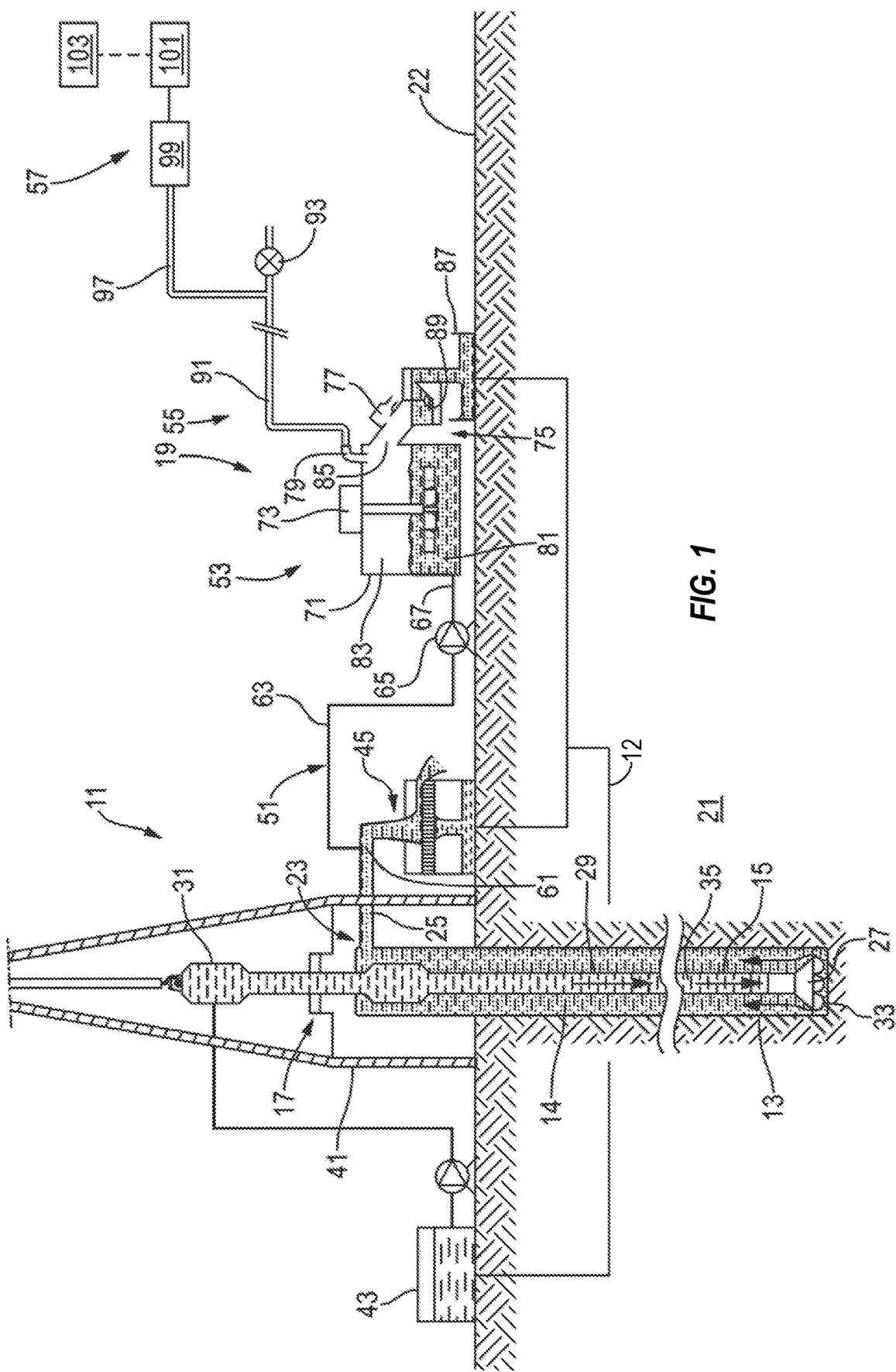
FIG. 1 is a schematic view of at least a portion of an example implementation of a drilling installation according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for simplicity and clarity, and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

As described above, variation in gas concentrations in drilling mud can be broadly attributed to drilling parameters, environment changes, formation fluid changes, and drilling fluid changes. Thus, identifying the effects of these variables, applying corrections, and removing artifacts may be performed during quality control processing before attempting mud gas interpretation. Reliable and quantitative mud gas data permits making real-time decisions about the hydrocarbon resource in the early stages of exploration and development.

Fluid Logging Analysis in Real Time ("FLAIR"), offered by Schlumberger, is a quantitative surface fluid logging tool which provides an accurate gas composition (lab quality) of the reservoir fluids during drilling. FLAIR data is primarily used for hydrocarbon and fluid contacts identification and inter- and intra-well fluid facies mapping. Gas composition from FLAIR may guide optimum sampling and downhole fluid analysis, as well as early detection of reservoir complexities (tight, thin layered, etc.). FLAIR is described herein as an example surface fluid logging tool. However, other gas analyzers may provide gas composition data that may be used as input data in the methods described herein.

FIG. 1 is a schematic view of at least a portion of an example implementation of a drilling installation 11 according to one or more aspects of the present disclosure. The drilling installation 11 pertains to a well for producing fluid, notably hydrocarbons, such as an oil well. The drilling installation 11 comprises a drilling conduit (e.g., casing) 13 positioned in a cavity 14 pierced by a rotary drilling tool 15, a surface installation 17, and an assembly 19 for analyzing gases contained in the drilling fluid.

The drilling conduit 13 is positioned in the cavity 14 pierced in the subsoil 21 by the rotary drilling tool 15. The drilling conduit 13 extends in an upper portion of the height of the cavity 14 which it delimits. The cavity 14 further has a lower portion directly delimited by the subsoil 21. The drilling conduit 13 includes at the surface 22 a well head 23 provided with a conduit 25 for circulation of the drilling fluid. The drilling tool 15 comprises, from bottom to top in FIG. 1, a drilling head 27, a drill string 29, and a head 31 for injecting drilling fluid. The drilling tool 15 is driven into rotation by the surface installation 17.

The drilling head 27 comprises a tool 33 for piercing the rocks of the subsoil 21. The drilling head 27 is mounted on the lower portion of the drill string 29 and is positioned at the bottom of the cavity 14. The drill string 29 comprises a set of hollow drilling tubes. These tubes delimit an inner space 35 which permits the drilling fluid injected through the head 31 to be conducted to the drilling head 27. For this purpose, the injection head 31 is screwed onto the upper portion of the drill string 29. The surface installation 17 comprises an apparatus 41 for supporting and driving into rotation the drilling tool 15, an apparatus 43 for injecting the drilling fluid, and a vibrating sieve 45. The injection apparatus 43 is hydraulically connected to the injection head 31 for introducing and circulating the drilling fluid in the internal space 35 of the drill string 29.

The drilling fluid is introduced into the inner space 35 of the drill string 29 through the injection apparatus 43. The drilling fluid flows downwards down to the drilling head 27 and passes into the drilling conduit 13 through the drilling head 27. The drilling fluid cools and lubricates the piercing tool 33. The drilling fluid collects the solid debris resulting from the drilling and flows upwards through the annular space defined between the drill string 29 and the walls of the drilling conduit 13, and is then discharged through the circulation conduit 25. The drilling fluid present in the cavity 14 maintains hydrostatic pressure in the cavity, which prevents breakage of the walls delimiting the cavity 14 not covered by the conduit 13, and which further avoids eruptive release of hydrocarbons in the cavity 14.

The circulation conduit 25 is hydraulically connected to the cavity 14, through the well head 23 in order to collect the drilling fluid from the cavity 14. The circulation conduit 25 may be formed by an open return line or by a closed tubular conduit. In the example implementation depicted in FIG. 1, the conduit 25 is a closed tubular conduit. The vibrating sieve 45 collects the fluid loaded with drilling residues which flow out of the circulation conduit 25 and separates the liquid from the solid drilling residues. The analysis assembly 19 comprises a device 51 for sampling the drilling fluid in the conduit 25, an extraction device 53 for extracting a gas fraction of the compounds contained in the drilling fluid, a device 55 for transporting extracted gas fractions, and an analysis device 57.

The sampling device 51 comprises a sampling head 61 immersed in the circulation conduit 25, a sampling conduit 63 connected upstream to the sampling head 61, a pump 65 connected downstream to the sampling conduit 63, and a supply conduit 67 connected to an outlet of the pump 65 for bringing the drilling fluid into the extraction device 53. The sampling device 51 also comprises an assembly (not shown) for heating the sampled fluid. The heating assembly may be positioned between the pump 65 and the extraction device 53 on the supply conduit 67, such as to permit heating the drilling fluid to a predetermined temperature facilitating extraction of gas compounds from the drilling fluid. The pump 65 may be a peristaltic pump capable of conveying the drilling fluid sampled by the head 61 towards the extraction device 53 with a determined fluid volume flow rate $Q_m$.

The extraction device 53 (hereinafter also called Flex) may comprise an enclosure 71 into which the supply conduit 67 discharges, a rotary stirrer 73 mounted in the enclosure 71, a mud discharge conduit 75, an inlet 77 for injecting a carrier gas, and an outlet 79 for sampling the extracted gas fractions in the enclosure 71. The enclosure 71 may have an inner volume of about 0.04-3 liters (L). The enclosure 71 defines a lower portion 81 and an upper portion 83. The lower portion 81 has an average volume $V_m$, which is kept substantially constant, and in which circulates the drilling fluid received from the supply conduit 67. The upper portion 83 has an average volume $V_g$, which is kept substantially constant, and which defines a gas head space above the drilling fluid. The mud supply conduit 67 discharges drilling fluid into the lower portion 81. The stirrer 73 is immersed in the drilling fluid present in the lower portion 81 and is operable to vigorously stir the drilling fluid in order to extract gases therefrom. The discharge conduit 75 extends between an overflow passage 85 made in the upper portion 83 of the enclosure 71 and a retention tank 87 intended to receive the drilling fluid discharged from the extraction device 53. The discharge conduit 75 is bent in order to form a siphon 89 opening out facing the retention tank 87 above the level of liquid contained in the retention tank 87. In some embodiments, the drilling fluid from the conduit 75 may be discharged into the circulation conduit 25.

In the example implementation depicted in FIG. 1, the carrier gas injection inlet 77 opens out into the discharge conduit 75 upstream from the siphon 89 in the vicinity of the overflow passage 85. In some embodiments, the inlet 77 may open out into the upper portion 83 of the enclosure 71. The sampling outlet 79 opens out into an upper wall delimiting the upper portion 83 of the enclosure 71. The drilling fluid introduced into the enclosure 71 via the supply conduit 67 is discharged by overflow into the discharge conduit 75 through the overflow passage 85. A portion of the discharged fluid temporarily lies in the siphon 89 to prevent gases from entering the upper portion 83 of the enclosure 71 through the discharge conduit 75. The introduction of gas into the enclosure 71 is therefore exclusively carried out through the inlet 77. In the example implementation depicted in FIG. 1, the carrier gas introduced through the inlet 77 is formed by the surrounding air around the installation 11, at atmospheric pressure. In some embodiments, the carrier gas may be another gas, such as nitrogen or helium.

In the implementation described above, an example of the extractor 53 has been disclosed in detail. However, other extractors permitting the extraction of gas from the drilling fluid may also or instead be used in relationship with the analysis device 57.

The transport device 55 comprises a line 91 for transporting the extracted gases toward the analysis device 57 and an apparatus 93 providing suction for conveying the gases extracted from the enclosure 71 through the transport line 91. The transport line 91 extends between the sampling outlet 79 and the analysis device 57. The transport line 91 has a length between about 10 meters (m) and about 500 m, such as may permit moving the analysis device 57 away from the well head 23 into a non-explosive area. The transport line 91 may be made of a metal or polymer material, such polyethylene and/or polytetrafluoroethylene (PTFE), among other examples.

The analysis device 57 comprises a sampling conduit 97 in fluid communication with the transport line 91 at a location upstream from the apparatus 93 providing suction, as well as a gas chromatography system 99 for separating the different compounds contained in the gas sample before the sample is analyzed. The analysis device 57 also comprises analyzing instrumentation 101 capable of detecting and quantifying the gas fractions extracted out of the drilling fluid in the enclosure 71 that have been transported through the transport line 91. The analyzing instrumentation 101 may comprise a mass spectrometer. Accordingly, online simultaneous detection and quantification of a plurality of compounds contained in the drilling fluid may be obtained, perhaps without manual sampling by a human operator.

Figure 13:
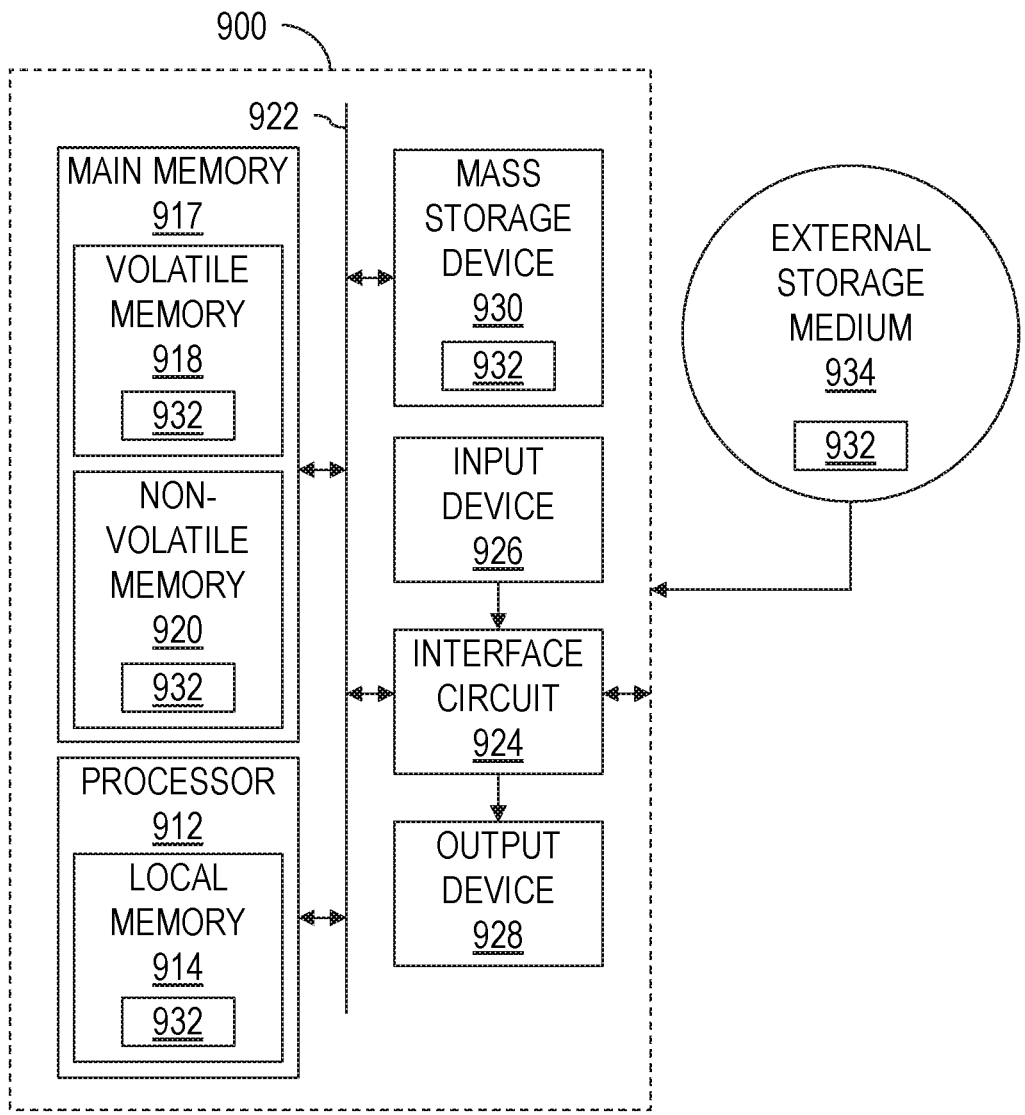
FIG. 13 is a schematic view of at least a portion of an example implementation of a processing system according to one or more aspects of the present disclosure.

The analysis system also comprises a computing unit 103 operable for determining the content of a plurality of compounds to be analyzed as being present in the drilling fluid, on the basis of the value of the extracted gas fractions in the enclosure 71, as determined by the instrumentation 101. The drilling fluid may be, for example, water-based mud, oil-based mud, or synthetic-based mud. The compounds to be analyzed contained in the drilling fluid are notably aliphatic or aromatic C1-C5 hydrocarbons. The computing unit 103, which may be situated at the well site and/or remotely, may comprise one or more processors for executing the calculations in combination with memory. FIG. 13, described below, is an example implementation of at least a portion of the computing unit 103.

Figure 2:
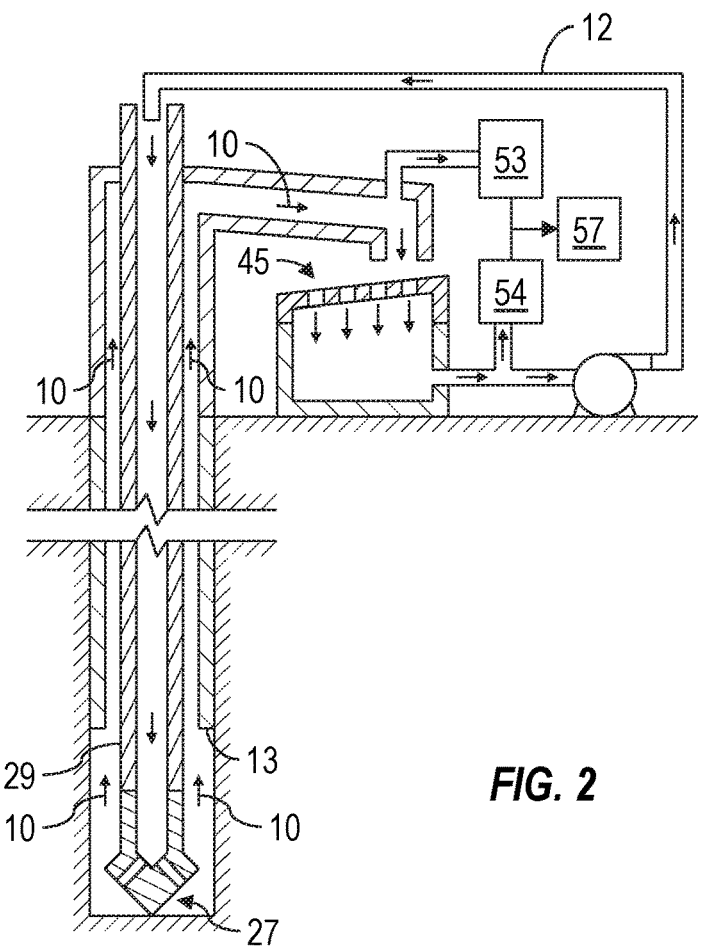
FIG. 2 is a simplified, schematic view of a portion of the apparatus shown in FIG. 1.

FIG. 2 is a simplified, schematic view of a portion of the drilling installation 11 depicted in FIG. 1. The following description refers to FIGS. 1 and 2, collectively. When providing the FLAIR service, an instance of the extractor 53 ("Flex Out") may be placed for analyzing the drilling fluid exiting the well (as indicated by arrows 10), while another instance 54 of the Flex extractor ("Flex In") is situated for analyzing drilling fluid in the flow line 12 between the mud pit (retention tank 87) and the injection apparatus 43, to collectively measure the amounts of C1-C5 hydrocarbons in the recycled mud and provide an estimation of the C1-C5 hydrocarbons coming exclusively from the formation 21 (by taking into account the contribution of the C1-C5 hydrocarbons entering the wellbore with a sample of drilling fluid when the analyzing the same sample at the exit of the wellbore). As described above, and as further described in U.S. Pat. No. 7,392,138, the entire disclosure of which being hereby incorporated herein by reference, the FLAIR device 57 is in communication with the Flex Out extractor 53 and the Flex In extractor 54 so as to provide quantitative measurement of the amounts of C1-C5 hydrocarbons in the drilling fluid exiting and entering the well.

When a hydrocarbon-bearing section is encountered during drilling, the drilling mud comes in contact with the reservoir fluid. The mud, carrying the hydrocarbon, flows back to the surface where it is processed and analyzed in the FLAIR unit 57. The fluid coming from the well and the fluid pumped back into the well are both processed to extract the gas components associated with hydrocarbon in the reservoir (as shown in FIGS. 1 and 2, described above). The gas is analyzed using gas chromatography and mass spectrometry to quantify the amount of methane (C1), ethane (C2), propane (C3), n-butane (nC4), iso-butane (iC4), n-pentane (nC5), and iso-pentane (iC5). The molar gas composition is matched with the depth from which the hydrocarbon originated during drilling. The molar composition of C1-C5 from FLAIR has been shown to be comparable to the normalized gas composition acquired from laboratory fluid analysis techniques. However, while the present disclosure refers to the molar composition of C1-C5 obtained from a FLAIR unit, other methods of surface analysis of drilling mud for obtaining the molar composition of C1-C5 are also within the scope of the present disclosure, and it is to be understood that reference herein to FLAIR also includes such other methods.

The present disclosure introduces a workflow for identifying the reservoir fluid type (e.g., black oil, gas condensate, or gas) directly from the gas composition obtained by a FLAIR unit. Such real-time fluid type identification may be used for making informed drilling decisions and planning sampling points, among other examples. The fluid type classification workflow uses FLAIR measurements in a statistical learning model to categorize the hydrocarbon fluid as black oil, gas condensate, or dry gas. Advanced statistical learning tools are used to build a classification model to accurately identify the fluid type with a given set of input parameters, such as molar gas composition (C1-C5 mol %). Statistical learning refers to a wide range of tools for exploring and understanding data through statistical models. The classification model is used for estimating/predicting an output based on one or more inputs. The classification model is trained with historical reservoir fluid data.

A database containing fluid properties of reservoir fluids was used to build, train, and validate the statistical models. The database contained 1000+ samples distributed into the three type of fluids (oil, gas condensate and gas). An exploratory data analysis technique was used to identify a set of relevant input parameters for the model. Input parameters were selected based on their respective influence on the classification accuracy of the model.

Figure 3:
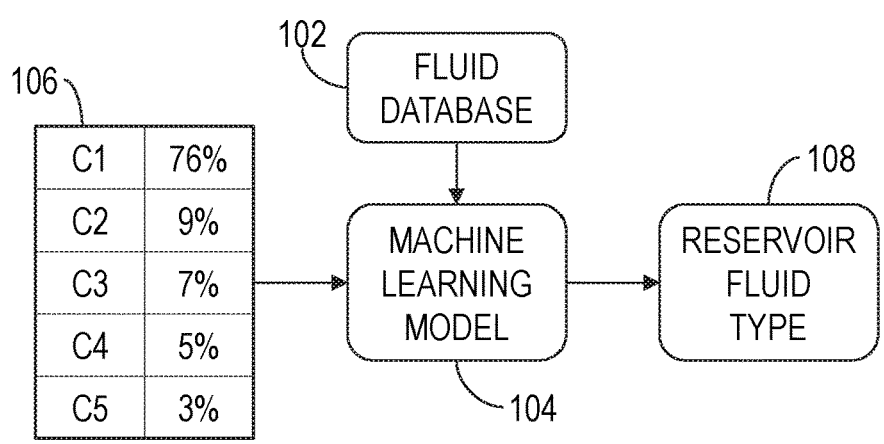
FIG. 3 is a block diagram of an example implementation of a methodology for generating a fluid type classification model according to one or more aspects of the present disclosure.

The database contained compositions of the light hydrocarbon (C1-C5 mol %) and associated fluid type (oil, gas condensate, and gas). To ensure data consistency, statistical tools (e.g., Mahalanobis distance) may be used to identify and remove outliers from the database. Composition mass balance may also be checked for the samples. After quality control, composition is normalized to 100% to make the data comparable to the compositions determined by the FLAIR unit. For fluid type identification, C1-C5 mol % are utilized as inputs (predictors) to the classification model. An example of such methodology is depicted in FIG. 3, in which the existing fluid database 102 is utilized to build and train the machine learning, fluid type classification model 104, which is then utilized with real-time FLAIR measurements 106 to predict the reservoir fluid type 108.

Two predictors, Wh and Bh as defined below in Equations (1) and (2), may be based on the ratios of C1, C2, C3, C4, and C5 mol %. The output of the model 104 is a categorical variable (response variable) corresponding to one of the three fluid types.

$$Wh = \frac{C2 + C3 + C4 + C5}{C1 + C2 + C3 + C4 + C5} \quad (1)$$

$$Bh = \frac{C1 + C2}{C3 + C4 + C5} \quad (2)$$

Other relevant measurements (e.g., lithology, gamma ray, resistivity, density, nuclear magnetic resonance, etc.) obtained during drilling may also be incorporated into the fluid-type classification if/when available. In this case, additional predictors based on these relevant measurements may be computed and used for the fluid type determination.

For generating and training the fluid type classification model, a Random Forest (RF) algorithm may be selected as the classification model. RF is a supervised learning model, a subclass of rule-based decision tree algorithm. Given a training dataset with input parameters and target classes, the decision tree algorithm generates a set of rules. These rules can then be used to predict the classes using the parameters from a new dataset. In RF, the model randomly selects predictors from the available input parameters to build decision trees and combines many decision trees into a single model. The model calculates the votes for each predicted target class and consider the class with the highest vote as the final prediction. However, other classification models, alone or in combination, may be chosen.

The samples in the preexisting database may be split for training and validation purposes. For example, 80% of the samples (randomly selected) may be utilized as a training set, and the remaining (20%) of the samples may be utilized for validation. However, other proportions may also be utilized within the scope of the present disclosure. The fluid type classification model may be trained using, for example, a cross-validation technique. The RF parameters (number of trees, etc.) may be optimized for improved performance with Bayesian Optimization (BO), grid search, random search, or stochastic gradient search. Generally, large ranges may be defined for each of the parameters to be optimized, then the algorithm may iteratively determine for the best combination of parameters that minimizes cross-validation error of the training data.

The workflow for training the model may use a hierarchical classification model with two sub-models to improve the accuracy of the fluid-type classification. The first sub-model may identify the fluid as "Oil" or "Gas Condensate/Gas" type. The samples identified as "Gas Condensate/Gas" may then be classified as "Gas Condensate" or "Gas" type using the second sub-model.

An example performance of the first sub-model is shown below in Table 1A as a confusion matrix (results in percentage).

TABLE 1A

| Fluid Type Classification Model Training Matrix | | |
|---|---|---|
| Oil | 100 | 0 |
| Gas Condensate/Gas | 0 | 100 |
| | Oil | Gas Condensate/Gas |

Thus, the model training accuracy was 100%. In the validation step, the prediction accuracy of the trained model was around 97%, as shown below as a confusion matrix in Table 1B.

TABLE 1B

| Fluid Type Classification Model Validation Matrix | | |
|---|---|---|
| Oil | 97.1 | 3.3 |
| Gas Condensate/Gas | 2.9 | 96.7 |
| | Oil | Gas Condensate/Gas |

The performance of the second sub-model is shown below in Table 2A (training) and Table 2B (validation).

TABLE 2A

| Gas Condensate vs. Gas Classification Sub-Model Training Matrix | | |
|---|---|---|
| Gas Condensate | 100 | 0 |
| Gas | 0 | 100 |
| | Gas Condensate | Gas |

TABLE 2B

| Gas Condensate vs. Gas Classification Sub-Model Validation Matrix | | |
|---|---|---|
| Gas Condensate | 75.8 | 19.2 |
| Gas | 24.2 | 80.8 |
| | Gas Condensate | Gas |

The model training accuracy was 100% and the prediction accuracy for validation was around 80%. The hierarchical classification model also generates the probability of each sample belonging to one of the three fluid classes.

Figure 4:
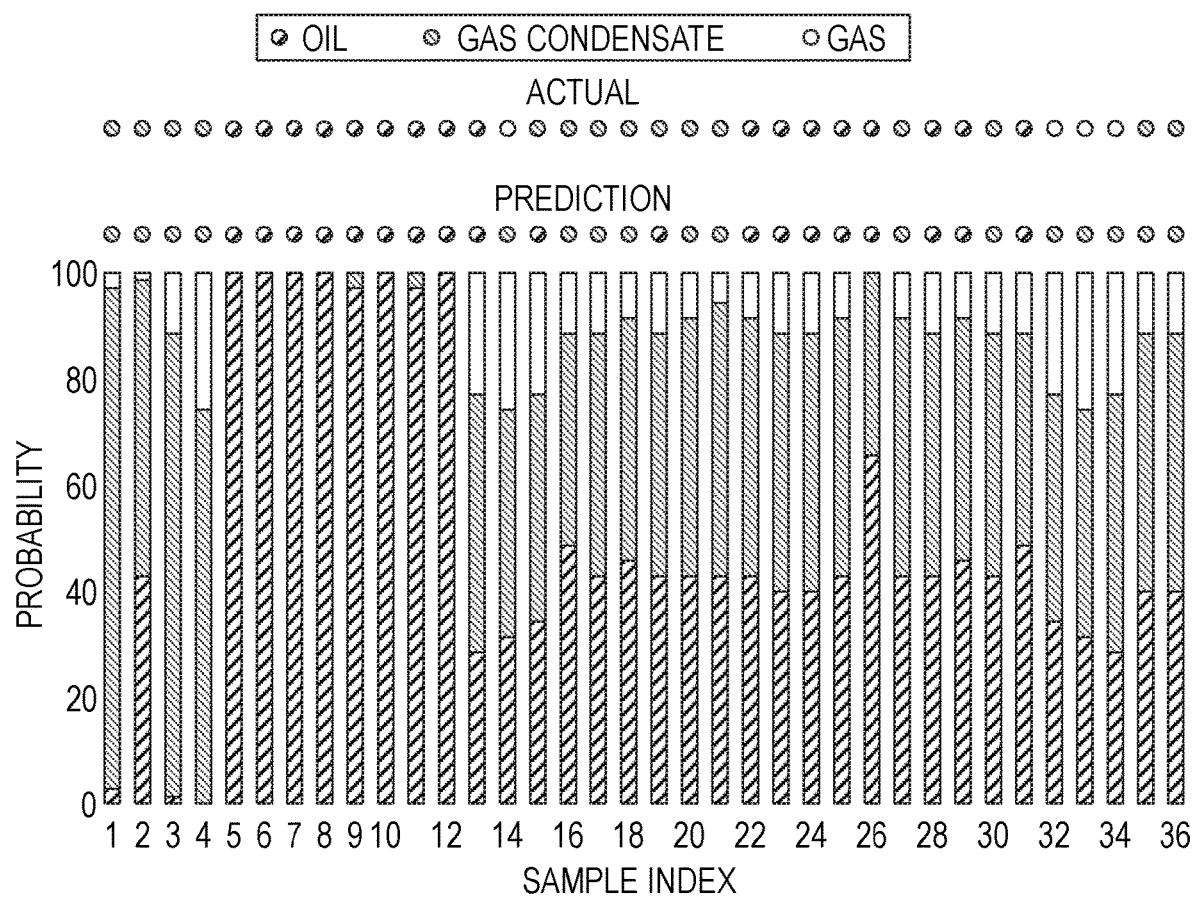
FIG. 4 is a bar chart depicting example model testing results according to one or more aspects of the present disclosure.

The performance of the trained models was tested using another dataset containing 51 fluid samples that were not used for model training. A portion of the results are depicted in FIG. 4 as a bar plot. All samples except 11 were correctly classified. Each test sample is represented in FIG. 4 by a vertical bar with associated probabilities (0 to 100%) of the sample belonging to each fluid type. The classification accuracy of this model was 78.0% on the test data. The performance is summarized in the confusion matrix set forth below in Table 3.

TABLE 3

Oil vs. Gas Condensate vs. Gas Classification Model Testing Accuracy Matrix

| | | | |
|---|---|---|---|
| Oil | 15 | 7 | 0 |
| Gas Condensate | 2 | 21 | 1 |
| Gas | 0 | 1 | 4 |
| | Oil | Gas Condensate | Gas |

Figures 5, 6:
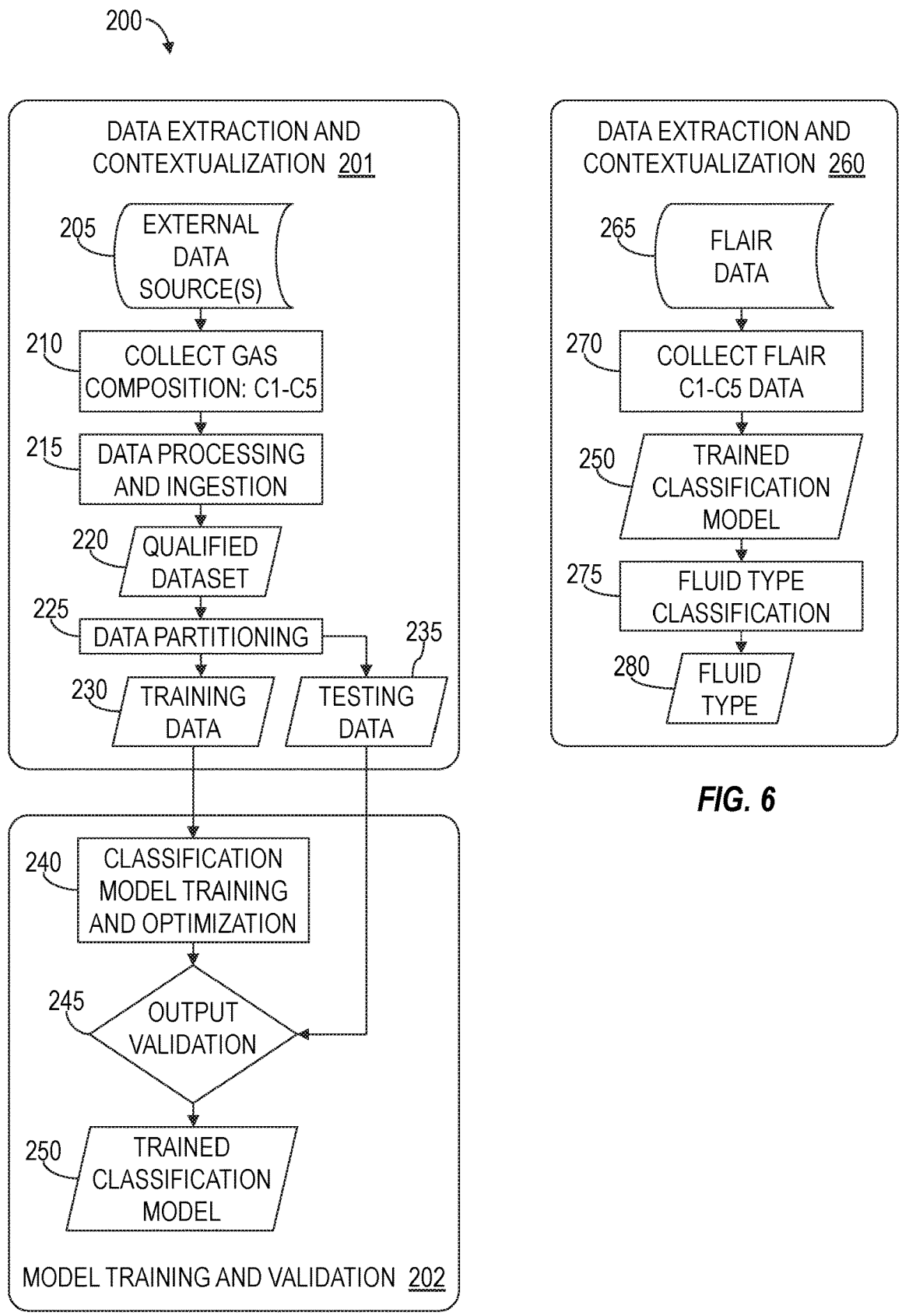
FIG. 5 is a flow-chart diagram of at least a portion of an example implementation of a method of generating a fluid type classification model according to one or more aspects of the present disclosure.
FIG. 6 is a flow-chart diagram of at least a portion of an example implementation of a method of using a fluid type classification model according to one or more aspects of the present disclosure.

FIG. 5 is a flow-chart diagram of at least a portion of an example implementation of the workflow 200 for generating the fluid type classification model. The workflow 200 is divided into two parts, namely, data extraction and contextualization 201 and model training and validation 202. The preexisting database 205 is accessed to collect 210 gas composition for C1-C5. The collected 210 data is processed and ingested 215, such as to remove outliers, check composition mass balances of the accessed samples, and normalize composition to 100% to make the data comparable to the compositions that will be determined by the FLAIR unit, thereby producing a qualified dataset 220. The qualified dataset 220 may then be partitioned 225 to designate a portion (e.g., 80%) for utilization as training data 230 and the remaining portion for utilization as testing/validation data 235. As described above, the training data 230 is then utilized for training (and optimization) 240—such as described above in relation to determining predictors and algorithm, etc.—and the testing data 235 is then utilized for validating output 240, thereby resulting in the trained fluid type classification model 250.

FIG. 6 is a flow-chart diagram of at least a portion of an example implementation of a method 260 for utilizing the trained fluid type classification model 250 to identify the fluid type of a new fluid in the field. For example, new fluid data 265 generated by the FLAIR unit 57 is utilized to collect 270 C1-C5 data of the new fluid. The collected C1-C5 data is used as input to the trained classification model 250 to classify 275 the new fluid in one of the three classes (oil, gas condensate, gas), thus determining 280 the fluid type of the new fluid in real-time.

After the validity of the classification 275 is established, the collected C1-C5 data and the corresponding fluid type output 280 can be added to the training data 230 to enrich subsequent iterations of the classification model 250 by reiterating at least a portion of the workflow 200 of FIG. 5. However, this step is optional, e.g., when an answer product user ("client") wants to train the model on their data (e.g., for a specific field), and the workflow may not generally include this step.

The workflow 200 and method 260 in FIGS. 5 and 6 may also be extended to include other subclasses of the three classes described above, such as light oil, medium oil, heavy oil, volatile oil, etc. Moreover, the methodology above has been described in the context of using just the FLAIR gas data of fluids for model training. However, the methodology may also permit incorporating other measurements, such as may also be utilized as input to improve classification capability when the preexisting database includes such other measurements.

The present disclosure also introduces a workflow to estimate, directly from FLAIR gas composition (e.g., C1-C5 hydrocarbon amounts or molar composition) during drilling, the relative amounts of heavier molecules present in the reservoir fluid. Here, the heavier molecules (C6+) are considered as one pseudo-group comprising organic molecules with six carbons, such as hexane and benzene, or more, such as heptane, etc., in the molecule. This group is referred to as C6+ fraction hereafter. The C6+ fraction is generally contained in the liquid phase of the reservoir fluid. Such real-time estimation of the heavy fractions of the fluid may be useful in making informed drilling decisions and planning sampling points, among other possible uses.

The workflow uses FLAIR gas measurements to estimate the relative concentration of the C6+ fraction (in mol %) in a hydrocarbon sample, such as based on Equation (3) set forth below.

$$C6+ (\text{mol }\%) = \frac{\text{number of moles of components in the } C6+ \text{ fraction}}{\text{total number of moles of all components in the hydrocarbon}} \quad (3)$$

Advanced statistical learning tools nay be utilized to build a model to predict relative molecular concentration of C6+ (in mol %) with a given set of input parameters, such as molar gas composition (C1-C5 mol %). Statistical learning refers to a wide range of tools for exploring and understanding data through statistical models. The present disclosure introduces a reliable model that has been developed by training the model with historical reservoir fluid data, conceptually similar to the methodology described above.

The preexisting database containing fluid properties of reservoir fluids may again be used to build, train, and validate the statistical models. Exploratory data analysis techniques are used to identify a set of relevant input parameters for the model. Input parameters are selected based on their respective influence on the classification accuracy of the model.

The training database contained composition of the light hydrocarbon (C1-C5 mol %) and associated C6+ mol %, GOR, and STO density. The C4 and C5 mol % include the normal alkanes and all isomers, respectively. To ensure data consistency, statistical tools (e.g., Mahalanobis distance) may be used to identify and remove outliers from the database. Composition mass balance may also be checked for the samples. After these quality control procedures, composition of the light hydrocarbons may be normalized to 100% to make the data comparable to FLAIR composition. The training database may be the same or different than the training database that has been described in relationship with the method of FIGS. 3-6.

Figure 7:
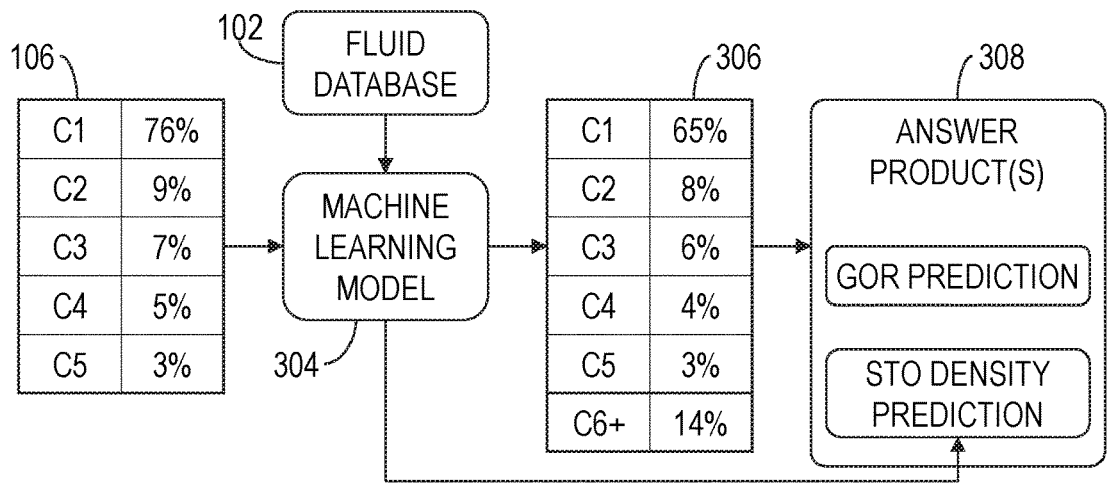
FIG. 7 is a block diagram of an example implementation of a methodology for generating a hydrocarbon resource characteristic prediction model according to one or more aspects of the present disclosure.

As schematically depicted in FIG. 7, the existing fluid database 102 is utilized to build and train the machine learning model 304, which is then utilized with real-time FLAIR measurements 106 to output continuous variables (response variables) corresponding to the input gas composition 106, including C6+ fraction 306 and/or another answer product 308 (e.g., GOR and/or STO density) that may also be based on the predicted C6+ fraction 306. Other relevant measurements (e.g., lithology, gamma ray, resistivity, density, nuclear magnetic resonance, etc.) obtained during drilling may also be incorporated into the workflow.

The C6+ mol % may be estimated based on the inputs of C1-C5 mol % from the FLAIR data stream. It should be noted that the FLAIR gas composition is normalized to total 100% (C1+C2+C3+C4+C5=100%), as depicted by input 106 in FIG. 7. In contrast, PVT sample composition includes the C6+ mol %. (i.e., C1+C2+C3+C4+C5+C6plus=100%). For this workflow, the C6+ mol % is separated from the PVT database, and the C1-C5 mol % are normalized to 100%, as described above, thereby making the sample composition in the PVT database equivalent to the FLAIR gas composition. This database, referred to as the FLAIR-equivalent database, is used for model development. For training purposes, 80% of the samples (randomly selected) are designated as a training set, and the remaining samples are assigned to a validation set. The model may be trained using a cross-validation technique, among other examples.

By using clustering techniques, two (or more) clusters are identified in the FLAIR-equivalent data (C1-C5 and C6+ mol %) via known or future-developed clustering techniques. Each sample in the FLAIR-equivalent data is associated with one of the clusters.

The RF technique (and/or others) is then utilized to build a model that can identify the cluster-type of each sample in the data using C1-C5 mol % as input. As described above, RF is a supervised learning model, a subclass of rule-based decision tree algorithms. Given a training dataset with input parameters and target classes corresponding to each of the clusters, the decision tree algorithm generates a set of rules. These rules can then be used to predict the classes using the parameters from a new dataset. C6+ mol % can be predicted with a reasonable accuracy within each cluster using C1-C5 mol % as input. Implementations within the scope of the present disclosure may also include combining the two C6+ predictions using, for example, a weighted method (e.g., C6+=(weight 1×C6_cluster1)+(weight2×_C6 cluster2)). The RF model is trained utilizing the FLAIR-equivalent database to optimize the hyperparameters. Unsupervised learning models, such as Gaussian Mixture model, may also be used to build the classification model.

Figure 8:
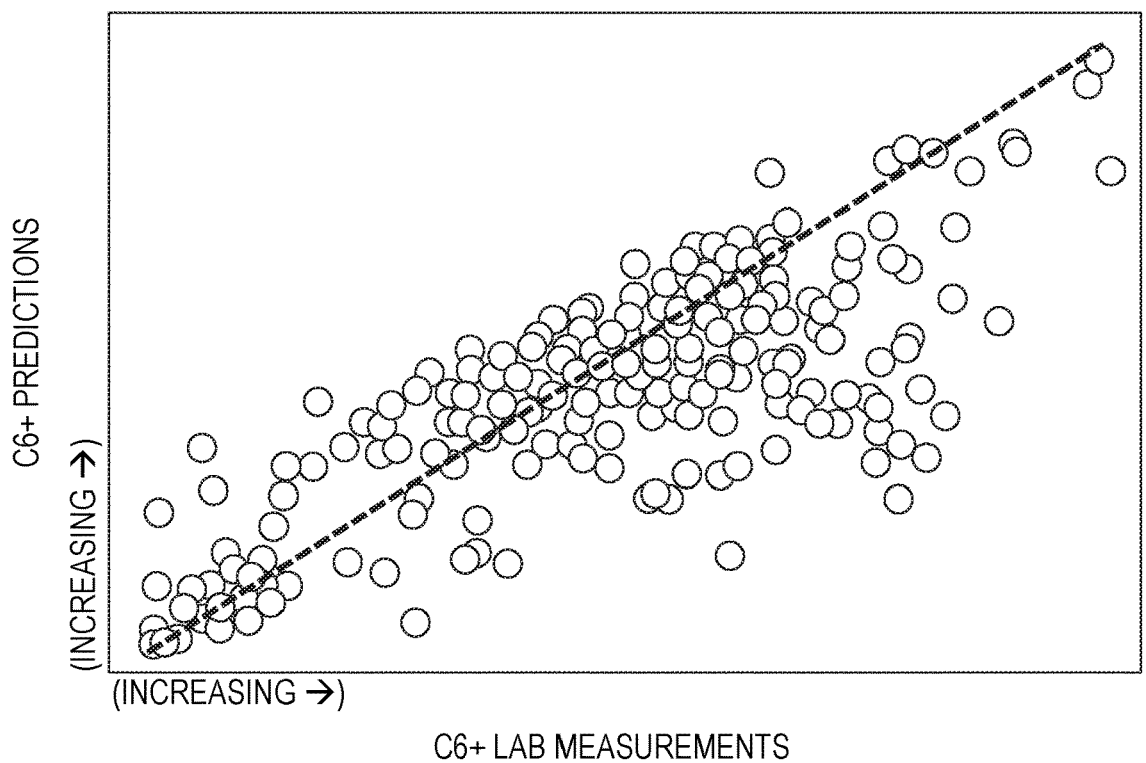
FIG. 8 is a graph depicting example results of C6+ predictions according to one or more aspects of the present disclosure.

Statistical models, such as regression models, are then developed for each cluster to predict C6+ mol % from C1-C5 mol %. Gaussian Process Regression (GPR) may be utilized to achieve good prediction accuracy. FIG. 8 shows a comparison of lab-measured C6+ mol % to the model-predicted values for samples in the validation set. An uncertainty estimate (mean +/−2*standard deviation) may also be generated for each C6+ prediction using the GPR. With the predicted value of C6+ mol %, the FLAIR predictions can be re-normalized so that C1-C6+=100%.

Figure 9:
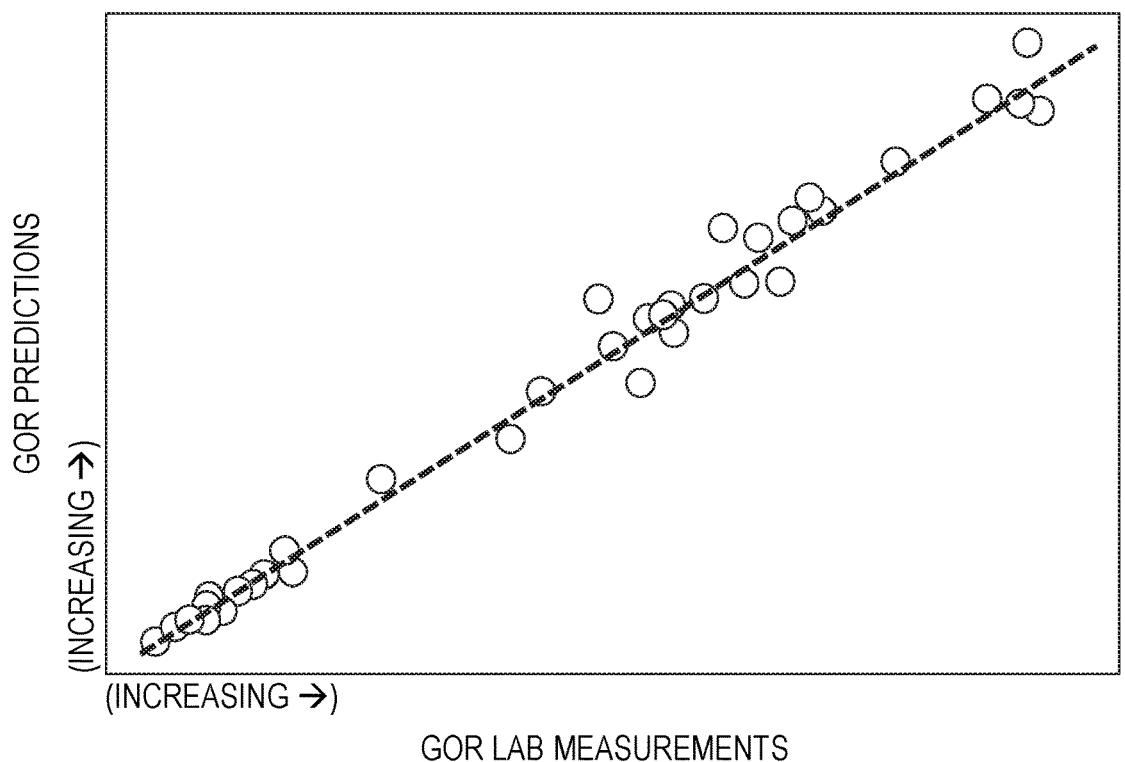
FIG. 9 is a graph depicting example results of GOR predictions according to one or more aspects of the present disclosure.

Another statistical model may be similarly generated to use the FLAIR gas composition and the predicted value of C6+ as input in order to predict GOR for that sample. Such statistical model is again specific to each cluster. That is, there is one GOR-predicting statistical model per cluster. FIG. 9 shows a comparison of lab-measured GOR to the model-predicted values.

Figure 10:
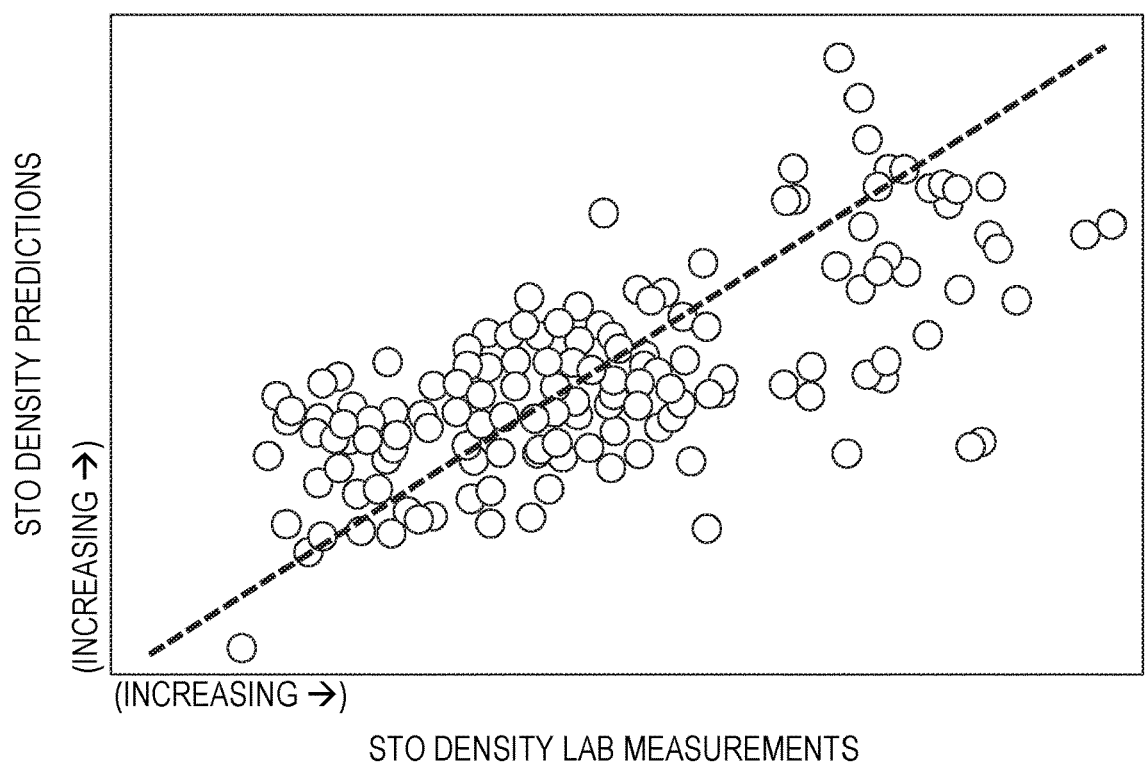
FIG. 10 is a graph depicting example results of STO density predictions according to one or more aspects of the present disclosure.

An independent statistical model may similarly be generated to predict STO density of a sample from the FLAIR-obtained C1-C5 mol %. FIG. 10 shows a comparison of lab-measured STO density to the model-predicted values. For this STO density version, the preliminary classification into one of the number of clusters may not be necessary, such that the statistical model may be applied directly on the entire training dataset.

Figure 11:
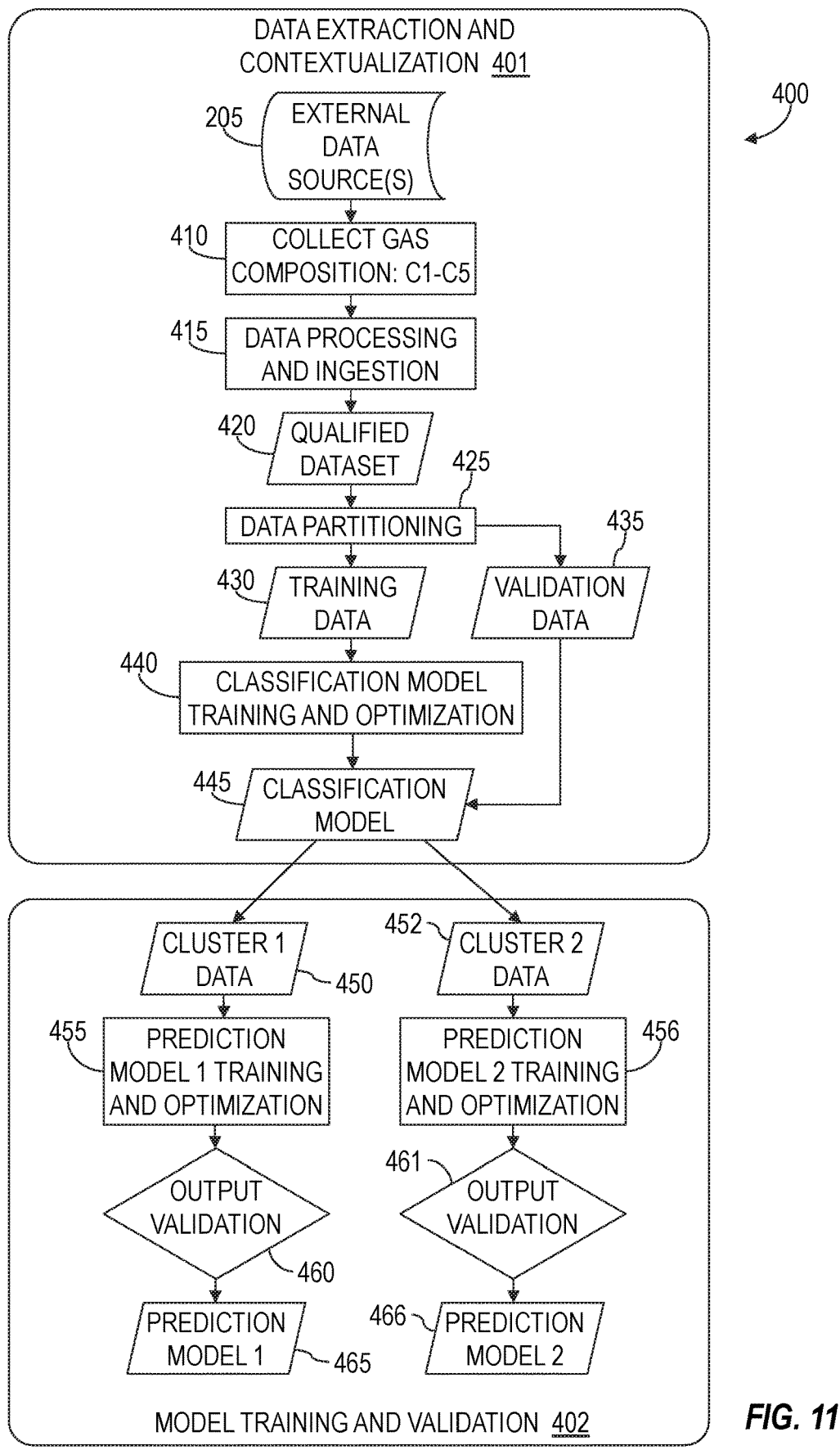
FIG. 11 is a flow-chart diagram of at least a portion of an example implementation of a method of generating a hydrocarbon resource characteristic prediction model according to one or more aspects of the present disclosure.

FIG. 11 is a flow-chart diagram of at least a portion of an example implementation of the workflow 400 for generating the hydrocarbon resource characteristic model described above. The workflow 200 is divided into two parts, namely, data extraction and contextualization 401 and model training and validation 402. The preexisting database 205 is accessed to collect 410 gas composition for C1-C5. The collected 410 data is processed and ingested 415, such as to remove outliers, check composition mass balances of the accessed samples, and normalize composition to 100% to make the data comparable to the compositions that will be determined by the FLAIR unit, thereby producing a qualified dataset 420. The qualified dataset 420 may then be partitioned 425 to designate a portion (e.g., 80%) for utilization as training data 430 and the remaining portion for utilization as testing/validation data 435.

As described above, the training data 430 is then utilized for training (and optimization) 440 to generate the cluster classification model 445. For example, clustering (e.g., unsupervised) may be performed on the training data 430. As mentioned above, the clusters are determined based on the similarity of the correlation between the inputs (normalized C1-C5) and the output (C6+). The classification model 445 may then be determined using a supervised technique, such as an RF technique. The classification model 445 sets rules to associate, for each gas sample/record, the input data (normalized C1-C5) to the corresponding cluster. The validation data 435 may then be used to validate the classification model 445, checking that each sample/record of the validation data 435 is associated with one of the clusters.

The validation data 435 of each cluster (450, 451) is then used to train and optimize 455, 456 a statistical (e.g., regression) prediction model 455, 456 specific to that cluster which, after validation 460, 461 (e.g., with the training data 430), provides the prediction models 465, 466 for each cluster. The prediction models 465, 466 may each comprise a model for predicting C6+ from the normalized C1-C5 for a corresponding one of the clusters. The prediction models 465, 466 may instead each comprise a model for predicting GOR from the normalized C1-C5 and the predicted C6+ for a corresponding one of the clusters. In other implementations, the method 400 may also provide a prediction model for STO density based on the C1-C5 normalized composition, whether for the entire dataset or, as for the C6+ and GOR, as valid for the data of a specific cluster.

Figure 12:
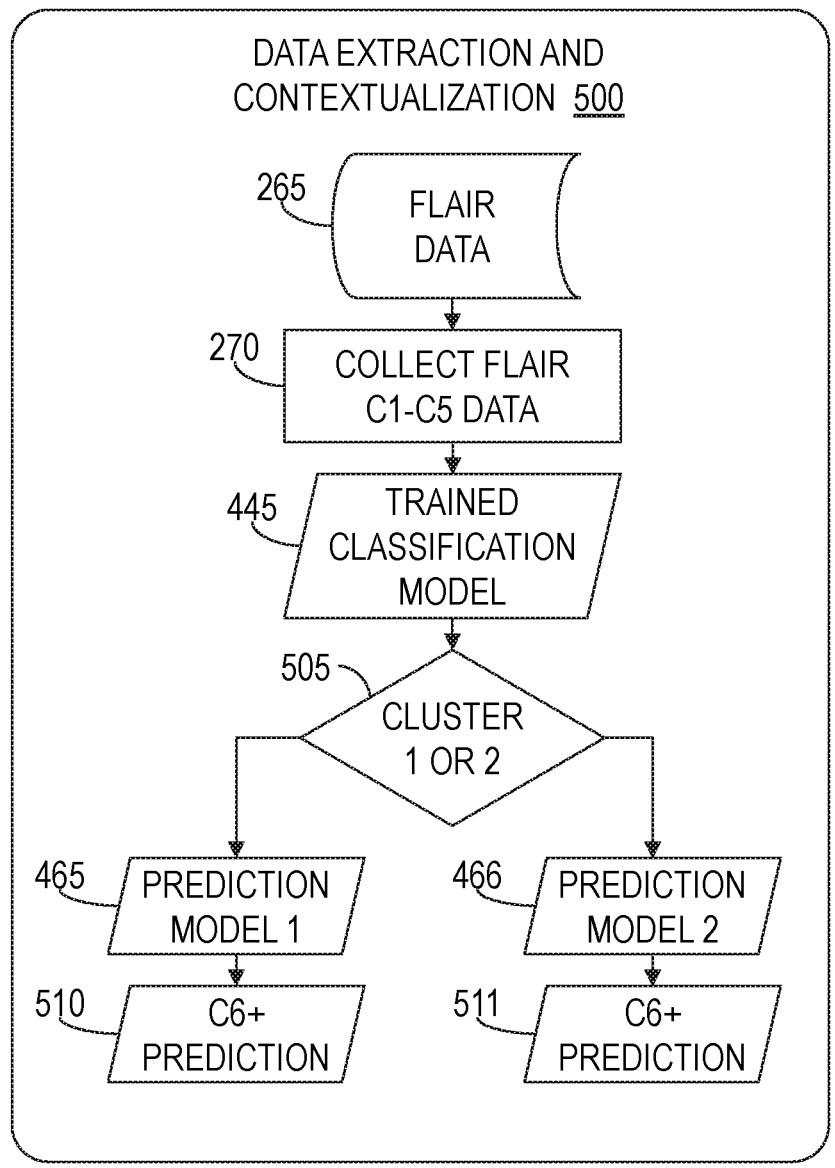
FIG. 12 is a flow-chart diagram of at least a portion of an example implementation of a method of using a hydrocarbon resource characteristic prediction model according to one or more aspects of the present disclosure.

FIG. 12 is a flow-chart diagram of at least a portion of an example implementation of a method 500 for utilizing the classification model 445 and one of the prediction models 465, 466 to predict a characteristic of a new fluid in the field. For example, the new fluid data 265 generated by the FLAIR unit 57 is utilized to collect 270 C1-C5 data of the new fluid. The collected C1-C5 data is used as input to the trained classification model 445 to classify 505 the new fluid into one of the clusters in real-time. The corresponding prediction model 465, 466 is then used to predict 510, 511 the C6+ fraction. Although not shown in FIG. 12, the GOR may then also be predicted utilizing the GOR- and cluster-specific prediction model 465, 466. STO density may also be obtained in parallel, based on the corresponding STO prediction model 465, 466, before or after the cluster classification 505.

After the validity of the classification 505, the C6+ prediction 510, 511, the GOR prediction, and/or the STO density prediction is established, the collected C1-C5 data and the corresponding prediction can be added to the training data 430 to enrich subsequent iterations of the models 445, 465, 466 by reiterating at least a portion of the workflow 400 of FIG. 11. However, this step is optional, e.g., when a client wants to train the model on their data (e.g., for a specific field) and the workflow may not generally include this step.

The workflows described above may be combined to generate estimates of fluid type, C6+ composition, and GOR based on advanced mud-gas data (C1-C5). The workflow provides a continuous fluid property log during drilling, generating the log as soon as the mud-gas data becomes available at the surface. Applications of the prediction workflows introduced herein may be utilized to enhance current mud gas interpretation for complex fluids (volatile oil/gas condensates) and identify fluid distribution and contacts, to aid reservoir fluid interpretation from petrophysical logs (e.g., gamma-ray, neutron-density porosity, resistivity, sonic, etc.), to support downhole sampling station selection for downhole fluid analysis tools during job planning, to provide fluid information in cases where direct fluid sampling is not feasible due to technical difficulty (e.g., small wellbore diameter), and/or for selection of well landing points and geo-steering using fluid information, among other purposes also within the scope of the present disclosure.

FIG. 13 is a schematic view of at least a portion of an example implementation of a processing system 900 according to one or more aspects of the present disclosure. The processing system 900 may execute example machine-readable instructions to implement at least a portion of one or more of the workflows, methods, and/or processes described herein, and/or to implement a portion of one or more of the example surface tools described herein. The processing system 900 may be or comprise, for example, one or more processors, controllers, special-purpose computing devices, servers, personal computers, personal digital assistant (PDA) devices, smartphones, internet appliances, and/or other types of computing devices.

The processing system 900 may comprise a processor 912, such as a general-purpose programmable processor, for example. The processor 912 may comprise a local memory 914 and may execute program code instructions 932 present in the local memory 914 and/or another memory device. The processor 912 may execute, among other things, machine-readable instructions or programs to implement the methods and/or processes described herein. The programs stored in the local memory 914 may include program instructions or computer program code that, when executed by an associated processor, cause a controller and/or control system implemented in surface equipment and/or a downhole tool to perform tasks as described herein. The processor 912 may be, comprise, or be implemented by one or more processors of various types operable in the local application environment, and may include one or more general-purpose processors, special-purpose processors, microprocessors, digital signal processors (DSPs), field-programmable gate arrays (FPGAs), application-specific integrated circuits (ASICs), processors based on a multi-core processor architecture, and/or other processors.

The processor 912 may be in communication with a main memory 917, such as via a bus 922 and/or other communication means. The main memory 917 may comprise a volatile memory 918 and a non-volatile memory 920. The volatile memory 918 may be, comprise, or be implemented by random access memory (RAM), static RAM (SRAM), dynamic RAM (DRAM), synchronous DRAM memory (SDRAM), RAMBUS DRAM (RDRAM), and/or other types of RAM devices. The non-volatile memory 920 may be, comprise, or be implemented by read-only memory, flash memory, and/or other types of memory devices. One or more memory controllers (not shown) may control access to the volatile memory 918 and/or the non-volatile memory 920.

The processing system 900 may also comprise an interface circuit 924. The interface circuit 924 may be, comprise, or be implemented by various types of standard interfaces, such as an Ethernet interface, a universal serial bus (USB), a third-generation input/output (3GIO) interface, a wireless interface, and/or a cellular interface, among other examples. The interface circuit 924 may also comprise a graphics driver card. The interface circuit 924 may also comprise a communication device, such as a modem or network interface card, to facilitate exchange of data with external computing devices via a network, such as via Ethernet connection, digital subscriber line (DSL), telephone line, coaxial cable, cellular telephone system, and/or satellite, among other examples.

One or more input devices 926 may be connected to the interface circuit 924. One or more of the input devices 926 may permit a user to enter data and/or commands for utilization by the processor 912. Each input device 926 may be, comprise, or be implemented by a keyboard, a mouse, a touchscreen, a trackpad, a trackball, an image/code scanner, and/or a voice recognition system, among other examples.

One or more output devices 928 may also be connected to the interface circuit 924. One or more of the output devices 928 may be, comprise, or be implemented by a display device, such as a liquid crystal display (LCD), a light-emitting diode (LED) display, and/or a cathode ray tube (CRT) display, among other examples. One or more of the output devices 928 may also or instead be, comprise, or be implemented by a printer, speaker, and/or other examples.

The processing system 900 may also comprise a mass storage device 930 for storing machine-readable instructions and data. The mass storage device 930 may be connected to the interface circuit 924, such as via the bus 922. The mass storage device 930 may be or comprise a floppy disk drive, a hard disk drive, a compact disk (CD) drive, and/or digital versatile disk (DVD) drive, among other examples. The program code instructions 932 may be stored in the mass storage device 930, the volatile memory 918, the non-volatile memory 920, the local memory 914, and/or on a removable storage medium 934, such as a CD or DVD.

The mass storage device 930, the volatile memory 918, the non-volatile memory 920, the local memory 914, and/or the removable storage medium 934 may each be a tangible, non-transitory storage medium. The modules and/or other components of the processing system 900 may be implemented in accordance with hardware (such as in one or more integrated circuit chips, such as an ASIC), or may be implemented as software or firmware for execution by a processor. In the case of firmware or software, the implementation can be provided as a computer program product including a computer readable medium or storage structure containing computer program code (i.e., software or firmware) for execution by the processor.

In view of the entirety of the present disclosure, including the figures and the claims, a person having ordinary skill in the art will readily recognize that the present disclosure introduces a method comprising obtaining input data regarding at least one measured property, wherein the at least one measured property includes an amount of each of a predetermined plurality of hydrocarbons in a gas sample extracted from drilling fluid after the drilling fluid exits a wellbore, and wherein the wellbore penetrates a subterranean formation comprising a hydrocarbon resource. The method also comprises predicting an unknown characteristic of an investigated fluid property of the hydrocarbon resource utilizing the obtained input data and one or more predetermined models each built via statistical classification and regression analysis of a preexisting database containing a plurality of records, wherein each record comprises known characteristics of a plurality of fluid properties of a different one of a plurality of known reservoir fluids, wherein the plurality of fluid properties comprises the investigated fluid property and the at least one measured property, and wherein the investigated fluid property comprises at least one of a fluid type of the hydrocarbon resource, an amount of at least one additional hydrocarbon, GOR, or STO density.

The one or more predetermined models may each have been: trained via statistical regression analysis of a first set of the records; and validated via statistical regression analysis of a second set of the records, wherein the second set of the records is exclusive of each of the first set of the records.

The unknown characteristic of the investigated fluid property may be which of a predetermined plurality of fluid types characterizes the hydrocarbon resource, the one or more predetermined models may be of just one predetermined model, and determining the unknown characteristic may comprise predicting that the hydrocarbon resource is one of the predetermined plurality of fluid types. The predetermined plurality of fluid types may be of black oil, gas condensate, and dry gas.

The unknown characteristic of the investigated fluid property may be a value for STO density.

The one or more predetermined models may include: a predetermined classification model; and a plurality of predetermined prediction models each specific to one of a plurality of predetermined clusters. Determining the unknown characteristic of the investigated fluid property may comprise: classifying the gas sample as one of the predetermined clusters by utilizing the obtained input data and the predetermined classification model; and determining the unknown characteristic of the investigated fluid property by utilizing the obtained input data and the one of the predetermined prediction models that is specific to the predetermined cluster in which the gas sample is classified. The predetermined clusters may be determined by performing unsupervised clustering of a first set of the records based on similarities of correlations between the predetermined plurality of hydrocarbons and the known characteristic of the investigated fluid property. The predetermined classification model may be determined by using a supervised technique that, for each of the first set of records, sets rules associating the amounts of each of the predetermined plurality of hydrocarbons of each of the first set of records to the corresponding cluster. The predetermined classification model may be validated using a second set of the records, exclusive of each of the first set of records, to confirm that each of the second records is associated with one of the predetermined clusters. For each predetermined cluster, the second set of the records corresponding to that predetermined cluster may be utilized to build the predetermined prediction model specific to that predetermined cluster.

The unknown characteristic of the investigated fluid property may be an amount or concentration of one or more additional hydrocarbons not included in the predetermined plurality of hydrocarbons. In such implementations, the predetermined plurality of hydrocarbons may be (e.g., may consist of) alkanes having less than six carbon atoms and the one or more additional hydrocarbons may be (e.g., may consist of) alkanes having more than five carbon atoms.

The unknown characteristic of the investigated fluid property may be a value for STO density.

The unknown characteristic of the investigated fluid property may be a first unknown characteristic of a first investigated fluid property, the predetermined classification model may be a first predetermined classification model, the plurality of predetermined clusters may be a plurality of first predetermined clusters, and the plurality of predetermined prediction models may be a plurality of first predetermined prediction models each specific to one of the first predetermined clusters. Determining the first unknown characteristic of the first investigated fluid property may comprise: classifying the gas sample as one of the first predetermined clusters by utilizing the obtained input data and the first predetermined classification model; and determining the first unknown characteristic of the first investigated fluid property by utilizing the obtained input data and the one of the first predetermined prediction models that is specific to the first predetermined cluster in which the gas sample is classified. The one or more predetermined models may further include: a second predetermined classification model; and a plurality of second predetermined prediction models each specific to one of a plurality of second predetermined clusters. The method may further comprise determining a second unknown characteristic of a second investigated fluid property by: (A) classifying the gas sample as one of the second predetermined clusters by utilizing the obtained input data and the second predetermined classification model; and (B) determining the second unknown characteristic of the second investigated fluid property by utilizing: (i) the obtained input data; (ii) the determined first unknown characteristic of the first investigated fluid property; and (iii) the one of the second predetermined prediction models that is specific to the second predetermined cluster in which the gas sample is classified. The predetermined plurality of hydrocarbons may be (e.g., may consist of) alkanes having less than six carbon atoms, the first unknown characteristic of the first investigated fluid property may be an amount or concentration of alkanes having more than five carbon atoms, and the second unknown characteristic of the second investigated fluid property may be a value for GOR.

Obtaining the input data may comprise: sampling the drilling fluid exiting the wellbore; extracting gas from the sampled drilling fluid using an extractor having constant volume; and analyzing the extracted gas to obtain the input data.

The method may further comprise: performing a drilling operation utilizing predetermined drilling parameters; and before or during performance of the drilling operation, adjusting one or more of the predetermined drilling parameters based on the predicted unknown characteristic of the investigated fluid property of the hydrocarbon resource.

The input data regarding an amount of each of a predetermined plurality of hydrocarbons may include molar gas composition of alkanes less than six carbon atoms.

The at least one measured property may include one of density, resistivity, lithology, or nuclear magnetic resonance.

The present disclosure also introduces a system comprising a processing system having a processor and memory storing program code instructions executable by the processor to: (A) receive input data regarding at least one measured property, wherein the at least one measured property includes an amount of each of a predetermined plurality of hydrocarbons in a gas sample extracted from drilling fluid after the drilling fluid exits a wellbore, and wherein the wellbore penetrates a subterranean formation comprising a hydrocarbon resource; and (B) predict an unknown characteristic of an investigated fluid property of the hydrocarbon resource utilizing: (i) the obtained input data; and (ii) one or more predetermined models each built via statistical classification and regression analysis of a preexisting database containing a plurality of records, wherein each record comprises known characteristics of a plurality of fluid properties of a different one of a plurality of known reservoir fluids, wherein the plurality of fluid properties comprises the investigated fluid property and the at least one measured property, and wherein the investigated fluid property comprises at least one of a fluid type of the hydrocarbon resource, an amount of at least one additional hydrocarbon, GOR, or STO density.

The system may further comprise: a sampling device operable to sample the drilling fluid exiting the wellbore; an extraction device operable to extract the gas sample from the sampled drilling fluid; and an analysis device operable for determining the amount of each of the predetermined plurality of hydrocarbons in the extracted gas sample. The gas sample may be a first gas sample, the input data may be first input data, the sampling device may be a first sampling device, the extraction device may be a first extraction device, the analysis device may be a first analysis device, and the system may further comprise: a second sampling device operable to sample drilling fluid entering the wellbore; a second extraction device operable to extract a second gas sample from the sampled drilling fluid entering the wellbore; and a second analysis device operable for determining the amount of each of the predetermined plurality of hydrocarbons in the second gas sample. The instructions may be further executable by the processor to: receive second input data regarding the at least one measured property of the second gas sample; and predict the unknown characteristic of the investigated fluid property of the hydrocarbon resource utilizing the first input data, the second input data, and the one or more predetermined models.

The unknown characteristic of the investigated fluid property may be which of a predetermined plurality of fluid types characterizes the hydrocarbon resource, the one or more predetermined models may be just one predetermined model, and determining the unknown characteristic may comprise predicting that the hydrocarbon resource is one of the predetermined plurality of fluid types. The predetermined plurality of fluid types may be (e.g., may consist of) black oil, gas condensate, and gas.

The unknown characteristic of the investigated fluid property may be a value for STO density.

The one or more predetermined models may include: a predetermined classification model; and a plurality of predetermined prediction models each specific to one of a plurality of predetermined clusters. Determining the unknown characteristic of the investigated fluid property may comprise: classifying the gas sample as one of the predetermined clusters by utilizing the obtained input data and the predetermined classification model; and determining the unknown characteristic of the investigated fluid property by utilizing the obtained input data and the one of the predetermined prediction models that is specific to the predetermined cluster in which the gas sample is classified. The unknown characteristic of the investigated fluid property may be an amount or concentration of one or more additional hydrocarbons not included in the predetermined plurality of hydrocarbons. The predetermined plurality of hydrocarbons may be (e.g., may consist of) alkanes having less than six carbon atoms, and the one or more additional hydrocarbons may be (e.g., may consist of) alkanes having more than five carbon atoms. The unknown characteristic of the investigated fluid property may be a value for STO density.

The unknown characteristic of the investigated fluid property may be a first unknown characteristic of a first investigated fluid property, the predetermined classification model may be a first predetermined classification model, the plurality of predetermined clusters may be a plurality of first predetermined clusters, and the plurality of predetermined prediction models may be a plurality of first predetermined prediction models each specific to one of the first predetermined clusters. The instructions may be further executable by the processor to determine the first unknown characteristic of the first investigated fluid property by: classifying the gas sample as one of the first predetermined clusters by utilizing the obtained input data and the first predetermined classification model; and determining the first unknown characteristic of the first investigated fluid property by utilizing the obtained input data and the one of the first predetermined prediction models that is specific to the first predetermined cluster in which the gas sample is classified. The one or more predetermined models may further include: a second predetermined classification model; and a plurality of second predetermined prediction models each specific to one of a plurality of second predetermined clusters. The instructions may be further executable by the processor to determine a second unknown characteristic of a second investigated fluid property by: classifying the gas sample as one of the second predetermined clusters by utilizing the obtained input data and the second predetermined classification model; and determining the second unknown characteristic of the second investigated fluid property by utilizing the obtained input data, the determined first unknown characteristic of the first investigated fluid property, and the one of the second predetermined prediction models that is specific to the second predetermined cluster in which the gas sample is classified. The predetermined plurality of hydrocarbons may be (e.g., may consist of) alkanes having less than six carbon atoms, the first unknown characteristic of the first investigated fluid property may be an amount or concentration of alkanes having more than five carbon atoms, and the second unknown characteristic of the second investigated fluid property may be a value for GOR.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same functions and/or achieving the same benefits of the embodiments introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. § 1.72(b) to permit the reader to quickly ascertain the nature of the technical disclosure. It is submitted with the understanding that it will not be used to interpret or limit the scope or meaning of the claims.

What is claimed is:

1. A method comprising:
   obtaining input data regarding at least one measured property, wherein the at least one measured property includes an amount of each of a predetermined plurality of hydrocarbons in a gas sample extracted from drilling fluid after the drilling fluid exits a wellbore, and wherein the wellbore penetrates a subterranean formation comprising a hydrocarbon resource; and predicting an unknown characteristic of an investigated fluid property of the hydrocarbon resource utilizing:
the obtained input data; and
one or more predetermined models each built via statistical classification and regression analysis of a preexisting database containing a plurality of records, wherein each record comprises known characteristics of a plurality of fluid properties of a different one of a plurality of known reservoir fluids, wherein the plurality of fluid properties comprises the investigated fluid property and the at least one measured property, and wherein the investigated fluid property comprises at least one of a fluid type of the hydrocarbon resource, an amount of at least one additional hydrocarbon, a gas-oil ratio (GOR), or a stock tank oil (STO) density; and
determining a first unknown characteristic of the investigated fluid property comprises:
classifying the gas sample as one of a first predetermined clusters of a plurality of predetermined clusters by utilizing the obtained input data and a first predetermined classification model; and
determining the first unknown characteristic of the first investigated fluid property by utilizing the obtained input data and one of a first predetermined prediction models that is specific to the first predetermined cluster in which the gas sample is classified;
determining a second unknown characteristic of a second investigated fluid properly by:
classifying the gas sample as one of a second predetermined clusters of the plurality of predetermined clusters by utilizing the obtained input data and a second predetermined classification model; and
utilizing the obtained input data, the determined first unknown characteristic of the first investigated fluid property, and one of a second predetermined prediction models that is specific to the second predetermined cluster in which the gas sample is classified.

2. The method of claim 1 wherein:
the unknown characteristic of the investigated fluid property is which of a predetermined plurality of fluid types characterizes the hydrocarbon resource;
the one or more predetermined models consist of just one predetermined model; and
determining the unknown characteristic comprises predicting that the hydrocarbon resource is one of the predetermined plurality of fluid types.

3. The method of claim 2 wherein the predetermined plurality of fluid types consists of black oil, gas condensate, and dry gas.

4. The method of claim 1 wherein the unknown characteristic of the investigated fluid property is a value for STO density.

5. The method of claim 1 wherein:
the one or more predetermined models include:
a plurality of predetermined prediction models each specific to one of the plurality of predetermined clusters;
determining the unknown characteristic of the investigated fluid property comprises:
classifying the gas sample as one of the predetermined clusters by utilizing the obtained input data and the predetermined classification model; and
determining the unknown characteristic of the investigated fluid property by utilizing the obtained input data and the one of the predetermined prediction models that is specific to the predetermined cluster in which the gas sample is classified.

6. The method of claim 5 wherein:
the predetermined clusters are determined by performing unsupervised clustering of a first set of the records based on similarities of correlations between the predetermined plurality of hydrocarbons and the known characteristic of the investigated fluid property;
the predetermined classification model is determined by using a supervised technique that, for each of the first set of records, sets rules associating the amounts of each of the predetermined plurality of hydrocarbons of each of the first set of records to the corresponding cluster;
the predetermined classification model is validated using a second set of the records, exclusive of each of the first set of records, to confirm that each of the second records is associated with one of the predetermined clusters; and
for each predetermined cluster, the second set of the records corresponding to that predetermined cluster is utilized to build the predetermined prediction model specific to that predetermined cluster.

7. The method of claim 5 wherein the unknown characteristic of the investigated fluid property is an amount or concentration of one or more additional hydrocarbons not included in the predetermined plurality of hydrocarbons.

8. The method of claim 7 wherein:
the predetermined plurality of hydrocarbons consists of alkanes having less than six carbon atoms; and
the one or more additional hydrocarbons consist of alkanes having more than five carbon atoms.

9. The method of claim 5 wherein the unknown characteristic of the investigated fluid property is a value for STO density.

10. The method of claim 5 wherein:
the predetermined classification model is a first predetermined classification model;
the plurality of predetermined clusters is a plurality of first predetermined clusters;
the plurality of predetermined prediction models is a plurality of first predetermined prediction models each specific to one of the first predetermined clusters;
the one or more predetermined models further include:
the second predetermined classification model; and
a plurality of second predetermined prediction models each specific to one of a plurality of second predetermined clusters.

11. The method of claim 10 wherein:
the predetermined plurality of hydrocarbons consists of alkanes having less than six carbon atoms;
the first unknown characteristic of the first investigated fluid property is an amount or concentration of alkanes having more than five carbon atoms; and
the second unknown characteristic of the second investigated fluid property is a value for GOR.

12. The method of claim 1 wherein obtaining the input data comprises:
sampling the drilling fluid exiting the wellbore;
extracting gas from the sampled drilling fluid using an extractor having constant volume; and
analyzing the extracted gas to obtain the input data.

13. The method of claim 1 further comprising:
performing a drilling operation utilizing predetermined drilling parameters; and
before or during performance of the drilling operation, adjusting one or more of the predetermined drilling parameters based on the predicted unknown characteristic of the investigated fluid property of the hydrocarbon resource.

14. The method of claim 1 wherein the input data regarding an amount of each of the predetermined plurality of hydrocarbons includes molar gas composition of alkanes less than six carbon atoms.

15. The method of claim 1 wherein the at least one measured property includes one of density, resistivity, lithology, or nuclear magnetic resonance.

16. A system comprising:
a processing system comprising a processor and memory storing program code instructions executable by the processor to:
  receive input data regarding at least one measured property, wherein the at least one measured property includes an amount of each of a predetermined plurality of hydrocarbons in a gas sample extracted from drilling fluid after the drilling fluid exits a wellbore, and wherein the wellbore penetrates a subterranean formation comprising a hydrocarbon resource; and
  predict an unknown characteristic of an investigated fluid property of the hydrocarbon resource utilizing:
    the received input data; and
    one or more predetermined models each built via statistical classification and regression analysis of a preexisting database containing a plurality of records, wherein each record comprises known characteristics of a plurality of fluid properties of a different one of a plurality of known reservoir fluids, wherein the plurality of fluid properties comprises the investigated fluid property and the at least one measured property, and wherein the investigated fluid property comprises at least one of a fluid type of the hydrocarbon resource, an amount of at least one additional hydrocarbon, a gas-oil ratio (GOR), or a stock tank oil (STO) density; and
  determine a first unknown characteristic of the investigated fluid property comprises:
    classifying the gas sample as one of a first predetermined clusters of a plurality of predetermined clusters by utilizing the obtained input data and a first predetermined classification model; and
    determining the first unknown characteristic of the first investigated fluid property by utilizing the obtained input data and one of a first predetermined prediction models that is specific to the first predetermined cluster in which the gas sample is classified;
  determine a second unknown characteristic of a second investigated fluid property by:
    classifying the gas sample as one of a second predetermined clusters of the plurality of predetermined clusters by utilizing the obtained input data and a second predetermined classification model; and
    utilizing the obtained input data, the determined first unknown characteristic of the first investigated fluid property, and one of a second predetermined prediction models that is specific to the second predetermined cluster in which the gas sample is classified.

17. The system of claim 16 further comprising:
a sampling device executable by the processor to sample the drilling fluid exiting the wellbore;
an extraction device executable by the processor to extract the gas sample from the sampled drilling fluid; and
an analysis device executable by the processor for determining the amount of each of the predetermined plurality of hydrocarbons in the extracted gas sample.

18. The system of claim 17 wherein:
the gas sample is a first gas sample;
the input data is first input data;
the sampling device is a first sampling device;
the extraction device is a first extraction device;
the analysis device is a first analysis device;
the system further comprises:
  a second sampling device executable by the processor to sample drilling fluid entering the wellbore;
  a second extraction device executable by the processor to extract a second gas sample from the sampled drilling fluid entering the wellbore; and
  a second analysis device executable by the processor for determining the amount of each of the predetermined plurality of hydrocarbons in the second gas sample; and
the instructions are further executable by the processor to:
  receive second input data regarding the at least one measured property of the second gas sample; and
  predict the unknown characteristic of the investigated fluid property of the hydrocarbon resource utilizing:
    the first input data;
    the second input data; and
    the one or more predetermined models.

19. The system of claim 16 wherein:
the unknown characteristic of the investigated fluid property is which of a predetermined plurality of fluid types characterizes the hydrocarbon resource;
the one or more predetermined models consist of just one predetermined model; and
determining the unknown characteristic comprises predicting that the hydrocarbon resource is one of the predetermined plurality of fluid types.

20. The system of claim 16 wherein:
the one or more predetermined model of the plurality of predetermined classification models; and
  a plurality of predetermined prediction models each specific to one of a plurality of predetermined clusters;
determining the unknown characteristic of the investigated fluid property comprises:
  classifying the gas sample as one of the predetermined clusters by utilizing the received input data and the predetermined classification model; and
  determining the unknown characteristic of the investigated fluid property by utilizing the received input data and the one of the predetermined prediction models that is specific to the predetermined cluster in which the gas sample is classified.

* * * * *